(12) United States Patent
Erikson et al.

(10) Patent No.: US 6,776,762 B2
(45) Date of Patent: Aug. 17, 2004

(54) PIEZOCOMPOSITE ULTRASOUND ARRAY AND INTEGRATED CIRCUIT ASSEMBLY WITH IMPROVED THERMAL EXPANSION AND ACOUSTICAL CROSSTALK CHARACTERISTICS

(75) Inventors: Kenneth R. Erikson, Henniker, NH (US); George K. Lewis, Andover, MA (US); Timothy E. White, Acton, MA (US)

(73) Assignee: BAE Systems Information and Electronic Systems Intergration Inc., Nashua, NH (US)

( * ) Notice: Subject to any disclaimer, the term of this patent is extended or adjusted under 35 U.S.C. 154(b) by 193 days.

(21) Appl. No.: 10/172,536

(22) Filed: Jun. 13, 2002

(65) Prior Publication Data

US 2003/0018267 A1 Jan. 23, 2003

Related U.S. Application Data (63) Continuation-in-part of application No. 10/094,851, filed on Mar. 8, 2002, now Pat. No. 6,589,180, and a continuation-in-part of application No. 09/969,438, filed on Oct. 2, 2001, now Pat. No. 6,524,254.
(60) Provisional application No. 60/299,634, filed on Jun. 20, 2001.

(51) Int. Cl.[7] ................................................. A61B 8/14
(52) U.S. Cl. ....................... 600/459; 29/25.35; 310/334
(58) Field of Search ................................ 600/407–472; 367/7, 11, 130, 138; 310/333, 334; 29/25.35; 73/625, 626

(56) References Cited

U.S. PATENT DOCUMENTS

| | | |
|---|---|---|
| 5,311,095 A | 5/1994 | Smith et al. |
| 5,329,498 A | 7/1994 | Greenstein |
| 5,381,067 A | 1/1995 | Greenstein et al. |
| 5,483,963 A | 1/1996 | Butler et al. |
| 5,732,706 A | 3/1998 | White et al. |
| 5,744,898 A | 4/1998 | Smith et al. |
| 5,957,851 A | 9/1999 | Hossack |
| 6,087,761 A | 7/2000 | Lorraine et al. |
| 6,159,149 A | 12/2000 | Erikson et al. |

OTHER PUBLICATIONS

PCT International Search Report dated Mar. 4, 2003 of International Application No. PCT/US02/18876 filed Jun. 13, 2002.

Primary Examiner—Ali Imam
(74) Attorney, Agent, or Firm—Maine & Asmus (57) ABSTRACT

An integrated piezoelectric ultrasound array structure configured to minimize the effects of differential thermal expansion between the array and the integrated circuit and to improve the mechanical and acoustical integrity of the array. The transducer array may have an interposed thinned supporting substrate and is matched to the integrated circuit substrate for thermal expansion so as to retain mechanical integrity of the array/IC bond within the working temperature range. Transducer elements are laterally isolated acoustically and as to thermal expansion by air or other acoustically attenuating medium of lower elastic modulus material between the elements. Acoustical effects are vertically acoustically isolated with capacitive coupling and small area solder bumps relative to wavelength, and further laterally acoustically isolated by thin supporting substrates relative to wavelength, including thinned semiconductor integrated circuit substrates.

24 Claims, 8 Drawing Sheets

PIEZOCOMPOSITE ULTRASOUND ARRAY AND INTEGRATED CIRCUIT ASSEMBLY WITH IMPROVED THERMAL EXPANSION AND ACOUSTICAL CROSSTALK CHARACTERISTICS

This application relates and claims priority for all purposes to now abandoned U.S. application Ser. No. 60/299,634, filed Jun. 20, 2001, and is a continuation in part to U.S. application Ser. Nos. 09/969,438, filed Oct. 2, 2001, now U.S. Pat. No. 6,524,254 and 10/094,851 filed Mar. 8, 2002, now U.S. Pat. No. 6,589,180.

FIELD OF INVENTION

This invention relates to the design and construction of piezocomposite ultrasound arrays in conjunction with integrated circuits, and in particular to improvements in thermal and crosstalk performance in piezocomposite ultrasound array and integrated circuit assemblies.

BACKGROUND OF THE INVENTION

Diagnostic ultrasound is an established and growing medical imaging modality. The configuration of a typical system includes a handheld probe connected to a host computer and image display unit by an umbilical cable carrying power, control signals and image data. Currently handheld probes using one-dimensional acoustical transducer arrays with up to 128 elements are the standard in the industry, although partial and full two dimensional arrays are well into development with several vendors.

Medical ultrasound systems transmit a short pulse of ultrasound and receive echoes from structures within the body. The handheld probes are most often applied to the skin using a coupling gel. Specialty probes are available for endocavity, endoluminal and intraoperative scanning. Almost all systems on the market today produce real-time, grayscale, B-scan images. Many systems include colorflow imaging.

Improved image quality requires the use of matrix (n×m) arrays with a thousand or more elements. As element numbers increase and their dimensions grow smaller, limitations to present fabrication technologies arise. Cost, ergonomics, produceability and reliability are important issues. Connecting an integrated circuit directly to the array elements alleviates these problems.

All linear arrays currently on the market use piezoelectric materials as the transducing mechanism from electrical signals to ultrasound (transmitter) and ultrasound back to electrical signals (receiver). The signals are generally in the form of short pulses or tone bursts.

Figure 1:
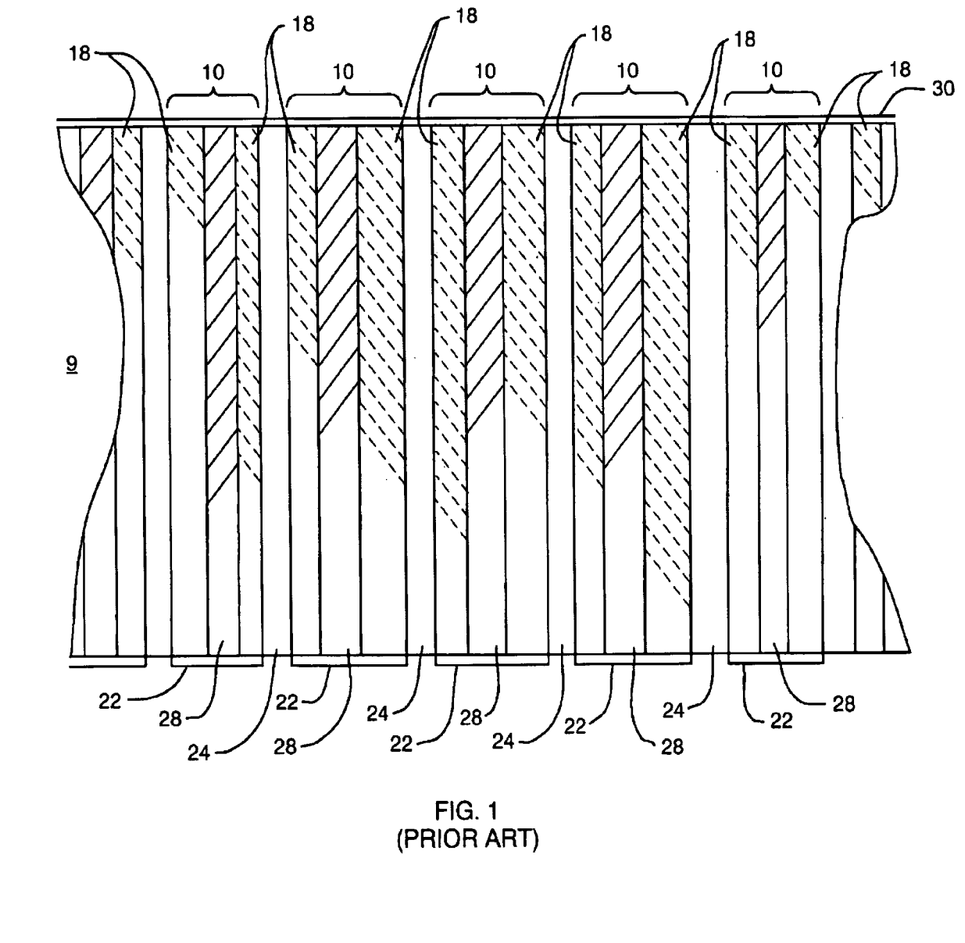
FIG. 1 is a prior art example, in diagrammatic cross-section, of a piezocomposite transducer array.

Referring to prior art FIG. 1, most high performance acoustical arrays use a piezocomposite material, which is fabricated by a "dice and fill" technique as is suggested, for example, in Smith et al's U.S. Pat. No. 5,744,898. The piezocomposite transducer array structure 9, having a planar array of piezocomposite transducer elements 10, provides improved bandwidth and efficiency as well as reduced crosstalk or interference between adjacent elements 10, relative to older designs.

Pieces of native ceramic such as Type 3203HD made by CTS Piezoelectric Products, or PZT-5H made by Morgan-Matroc, are diamond sawed in a crosscut pattern to yield pillars 18, there being multiple pillars in each piezocomposite element 10. The intra-element spaces 28 between the pillars are filled with a polymer, such as DER332 epoxy made by Dow Chemical. The inter-element spaces 24 are often left air-filled or are filled with a sound-absorbing polymer. Top electrode 30 is the common electrical connection between elements 10. Bottom electrodes 22 are delineated for each array element 10 and are used as the electrical connections to the piezocomposite material.

In a beamsteered transducer array, the dimensions of elements 10 are typically less than a wavelength (in water or tissue) in the steering dimension. For example, in a 3.5 MHz (1×128) array the element width is between 0.2 to 0.4 mm with a center to center spacing of 0.5 mm for a total array length of approximately 64 mm. In the other dimension, the element dimensions are a tradeoff between resolution and depth of focus. For a 3.5 MHz array, this dimension is typically 12 to 15 mm.

As the frequency of the array increases, element size decreases, as does element thickness, however, the aspect ratio remains constant. Other methods of fabrication such as laser milling or scribing, etching or deposition are under development. At present, they are not well accepted.

As is more fully described in the parent applications, in a fully assembled transducer scanner head, there is a backing behind the array and its supporting ASIC that provides mechanical support and acoustical attenuation. When a piezoelectric transducer is electrically pulsed, two acoustical pulses are generated that travel in opposite directions. The pulse traveling out of the scanhead is desired, while the pulse propagating into the backing is unwanted and is absorbed by the backing.

One or more matching layers are placed in the scanner head in the path of the desired pulse, to improve the coupling of energy from the piezocomposite into the body of the subject by matching the higher acoustical impedance piezocomposite to the lower acoustical impedance of the body. This matching layer functions in the same way as the anti-reflection coating on an optical lens.

The system electronics focus the pulse in the scanning plane dimension. A simple convex lens forms the front surface of the scanner head that contacts the patient's skin. It provides a fixed focus to the sound pulse in the "out-of plane" dimension, which is perpendicular to the scanning plane.

Modern systems impose increasingly stringent requirements on the acoustical arrays. Parameters that characterize typical medical ultrasound arrays are described in more detail in the parent applications, but with regard to this disclosure include in particular; crosstalk. Crosstalk is the interference of signals between array elements 10. The interference may be electrical, mechanical or acoustical. It is expressed in dB relative to the nearest neighbor element. Crosstalk in a well-constructed array is better than −30 dB.

Extension of the several inherent technologies to matrix transducer arrays is underway at most transducer and system manufacturers. As the number of elements increases and their size decreases, however, the existing approaches may no longer be feasible or practical. Processing time, touch labor, yield, reliability and cost become limiting issues and new processes are required.

Figure 2:
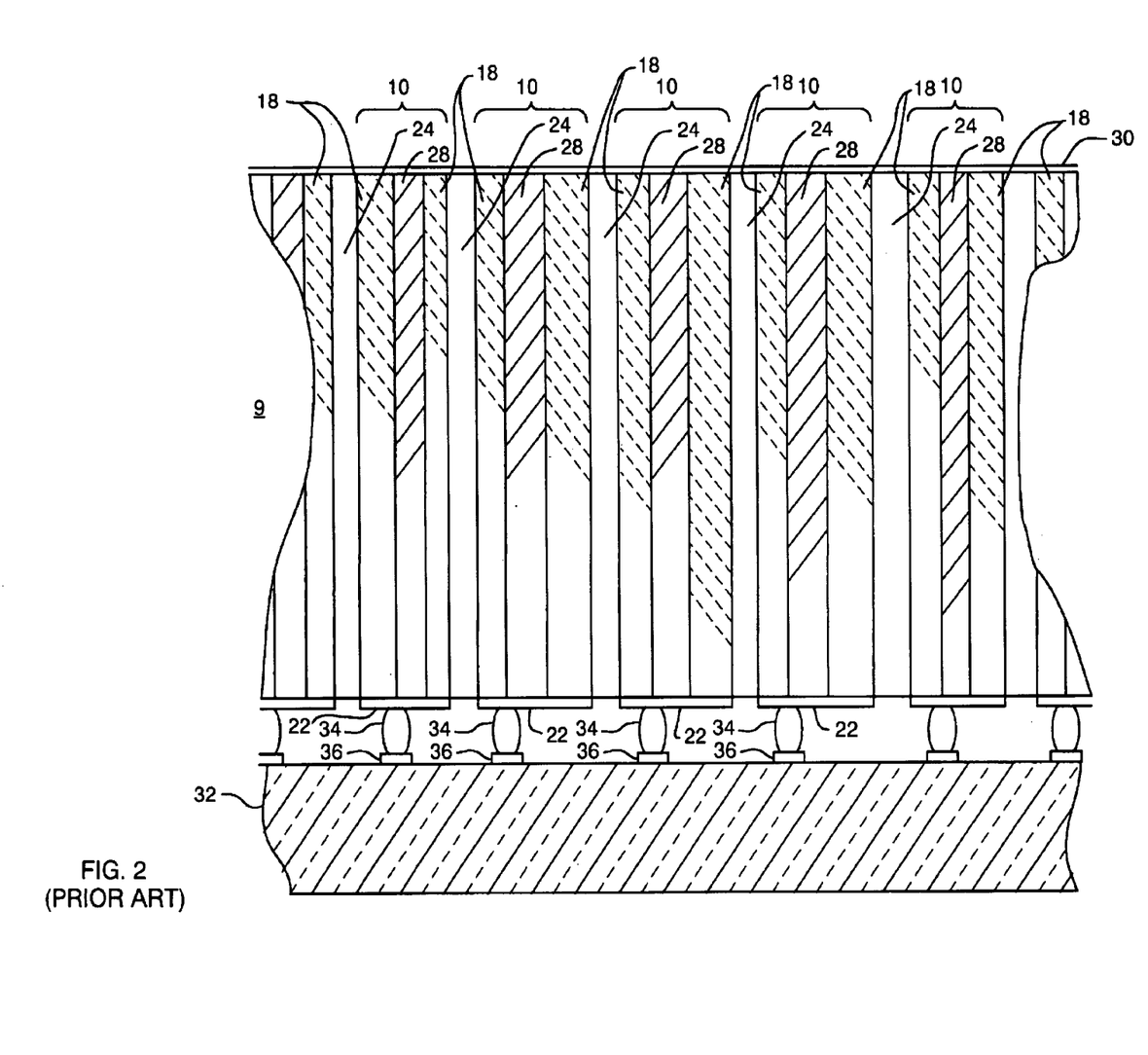
FIG. 2 is a prior art example, in diagrammatic cross-section, of a piezocomposite transducer array bump bonded to a semiconductor integrated circuit.

In FIG. 2, a cross-section of a prior art piezocomposite integrated array, the array elements 10 are electrically and mechanically connected to integrated circuit (IC) substrate 32 with electrically conductive bumps 34 using metallized pads 36 on IC 32 to form a complete electrical circuit. Integrated circuit substrate 32 is typically composed of silicon, although other semiconductors may be used. Conductive bumps 34 may be composed of solder or a conductive polymer such as silver epoxy.

Placing an integrated circuit (IC) directly behind an ultrasound array is a well-known solution to the problem of many long cables connecting the array elements in a scanhead to electronics in a separate electronics console. The preferred method places an IC with unit cells of similar dimensions to the array elements 10 immediately behind the array elements. The corresponding elements and unit cells are bonded electrically and mechanically to the IC using micro-solder balls. The space between the IC and the array can be filled with a material such as epoxy for improved mechanical strength. However, this leads to excessive crosstalk (signal interference) between the array elements. Crosstalk leads to poor dynamic range and loss of contrast in the images.

One solution to this problem is simply to leave an air space between the array and IC. The air gap effectively prevents sound transmission into the IC. By limiting the contact area to the micro solder balls alone, which area is much smaller than the wavelength of sounds, crosstalk is effectively eliminated. Use of an air gap, however, results in a relatively narrow bandwidth transducer array, typically with 30 to 60% fractional bandwidth. Modern medical ultrasound systems require bandwidths of 100 to 120%.

In a United States government agency funded program, a real-time, 3D, ultrasound camera intended for Army medic use on the front lines was designed and its feasibility proven. In this camera, an acoustical lens was used to image a volume onto a 128×128 (16,384 element), 5 MHz matrix array. Each element of the piezocomposite array had a custom integrated circuit bump-bonded directly behind it using micro-solder balls. The piezocomposite array was air-backed, i.e. there was a small air space between the array and the IC. The inter-element spaces were filled with polymer. The bump bonds were the only mechanical and electrical connections between the array and the IC. No matching layer was used on the front side of the array.

Each unit cell of the ROIC contained a preamplifier, signal processing, a limited amount of sampled data storage and multiplexing. The silicon was two side-buttable, permitting tiling of four pieces into the square 128×128 array. This integrated matrix array had several important limitations: It operated as a receiver only. The array bandwidth was only 35%, which is too low for use in most other ultrasound systems, although it was adequate for the camera, in which the multiplexing is significantly different from that used by beamformed B-scan ultrasound systems. Array crosstalk was marginally acceptable and reliability was poor. These problems were traced to differential thermal expansion between the piezocomposite array and the IC.

Referring to FIG. 2, the thermal expansion of the piezocomposite structure 9 in the plane of the array is determined by the combination of thermal expansion of the ceramic of pillars 18 and the epoxy in spaces 24 and 28. For example, PZT-5H, a typical piezo ceramic has a coefficient of thermal expansion (CTE) of $4 \times 10^{-6}$ per degree C., whereas DER 332, a typical epoxy, has a CTE of $40 \times 10^{-6}$ per degree C. or ten times that of the ceramic. Thus, the thermal expansion of a piezocomposite in the plane of the array is dominated by the epoxy. The CTE of silicon is about $7 \times 10^{-6}$ per degree C., which is a factor of five smaller than such a piezocomposite.

Temperature changes cause piezocomposite array 9 to expand or contract at a different rate than integrated circuit 32. Bump bonds 34 are stressed by these differential expansions. This stress may cause the bumps to rip apart. The adhesion at the interface between the bumps 34 and the array element electrodes 22 or at the integrated circuit pads 36 may also fail. One or more of the array elements 10 then becomes electrically and mechanically separated from the integrated circuit and the array becomes impaired or nonfunctional. As the size of the array increases to larger numbers of elements, the effect of the differential thermal expansion becomes worse. A five degree C. temperature change may be enough to cause failure. In the extreme, the array may even separate from the integrated circuit completely.

Clearly, there is a need for improved thermal performance while maintaining or improving acoustical isolation to reduce crosstalk and related interference between array elements.

SUMMARY OF THE INVENTION

It is among the goals of the invention to provide a piezocomposite transducer array and integrated circuit (IC) assembly that has better lateral acoustical isolation between transducer elements. It is another goal to provide a transducer array and IC assembly with improved mechanically reliability at the solder bond join between the array and the IC. It is also a goal to provide for greater vertical attenuation of acoustical signals as between the array and the IC.

It is an additional goal to provide a common electrode for the distal end of the elements of the array that combines acoustical matching properties suitable to the frequency of the array and the medium to which it is being applied.

To these ends, the invention includes a piezocomposite ultrasound array with approximately matched thermal expansion characteristics to silicon or other semiconductor material from which IC's are commonly constructed. The invention enables present fabrication techniques to be extended to larger and multi-dimensional arrays while maintaining the desirable properties of piezocomposite arrays such as high sensitivity, low crosstalk and relatively easy fabrication.

One aspect of the invention is the combination of a supporting substrate of the same thermal expansion characteristics as the IC, attached directly to the base end of the transducer elements so as to hold them in thermal alignment with the IC which is bump bonded with micro solder balls to the underside of the supporting substrate, thereby limiting the mechanical shear stress on the bump bonds caused by differential thermal expansion. The material in the spaces between the elements is selected to absorb the excess thermal expansion of the individual piezocomposite elements, so that the array as a whole can be constrained to the desired rate of expansion.

Another aspect of the invention provides for combining the elements of the first aspect with a common electrode layer at the distal end of the array elements that is configured to be an acoustical matching layer between the array the medium to which it is being applied.

Yet another aspect of the invention is the use of a thinned integrated circuit, or multiple thinned layers of integrated circuit, in an integrated ultrasound transducer array, which thus becomes essentially acoustically transparent. This technique minimizes crosstalk transmission through the IC and enables wide bandwidth transducers. Acoustical transparency requires the thickness of the IC to be selected to produce a minimum reflection at or near the center or midrange frequency of the transducer array. A thinned IC also permits the use of conventional ultrasound transducer designs including acoustically attenuating backing structures bonded to the IC, which are well known in the ultrasonic transducer art.

Other and additional goals and advantages of the invention will be apparent to those skilled in the art upon review of the abstract, description, figures and claims that follow.

DESCRIPTION OF THE PREFERRED EMBODIMENT

Figure 3:
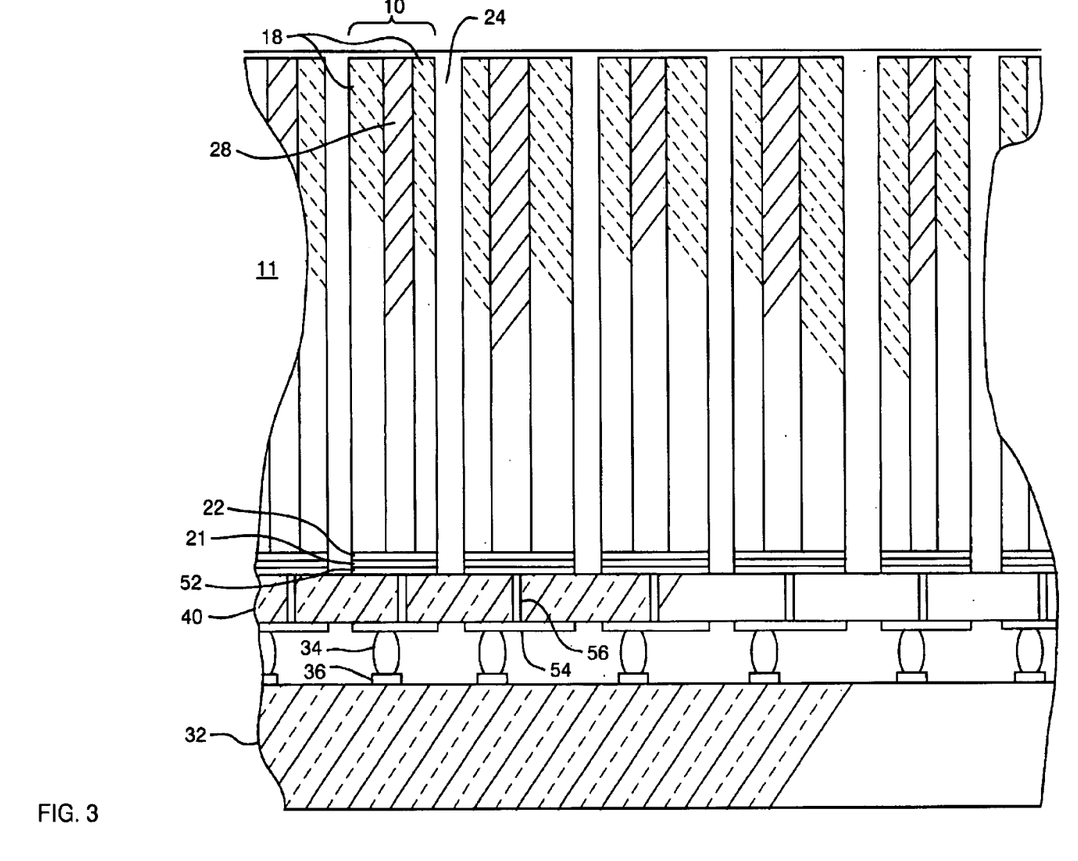
FIG. 3 is a diagrammatic cross-section view of a first embodiment of the invention, showing a thinned, interposed substrate bonded to a transducer array so as to establish the total thermal expansion rate of the array and to attenuate the vertical and lateral transmission path of acoustical signals from one element to the next.

The invention is susceptible of various embodiments, all within the scope of the description, figures and claims that follow. For example, FIG. 3 is a cross-sectional schematic of a preferred embodiment of an athermal piezocomposite array 11 using an interposed substrate 40, with a CTE (coefficient of thermal expansion) that matches the CTE of the integrated circuit 32 to support the plurality of individual array elements 10. Substrate 40 may, for example, be aluminum nitride, a ceramic with a CTE that closely matches silicon. Within each individual array element 10, epoxy is used in spaces 28 to hold the individual piezoceramic vertical members or pillars 18 together, as previously depicted in FIG. 2. Spaces 24 between elements 10 are left air-filled; air being highly elastic and sufficiently sound attenuating. Other gases, fluids or materials such as aerogels with similar properties, that are otherwise benign with respect to the other materials of the array, may be used. In other embodiments, spaces 24 may be filled with a material that possesses the correct acoustical and elastic properties and a CTE preferably less than that of silicon.

Thermal expansion greater than that of substrate 40 still occurs within an individual array element 10, due mainly to the much greater CTE of the epoxy in spaces 28, however the expansion is no longer cumulative across the array because it is offset by less expansion of the material within the inter-element spaces 24. Thus, the mechanical stability and the reliability of the structure, in particular the bump bonded solder joints between the array 11 and the integrated circuit 32, are improved by this technique.

Metallization top and bottom pads 52 and 54 are produced by photolithography, laser scribing or an equivalent method at the spacing of the array elements. Vias 56 are made by mechanical or laser drilling, wet-process, reactive-ion etching, or other well-known hole fabrication techniques. Electrical connections between pads 52 and 54 through vias 56 are established by conductive plating, conductive epoxy or inserting fine wires. Other established semiconductor fabrication methods including growing an electrically conductive polysilicon layer may also be used, so as to complete the network of electrical paths or vias from top to bottom through interposed substrate 40.

Substrate 40 is mechanically attached to each array element 10 at respective pads 52 and electrodes 22 with a layer 21 of material which in one preferred embodiment is a conductive silver epoxy. Alternatively, layer 21 may be a very thin layer of electrically non-conductive epoxy, which forms with metallic pads 52 and 22 a parallel plate capacitor. The electrical impedance of this interface at the array frequency is by design small enough that an acceptable RF electrical connection between bottom electrode 22 of array elements 10, and conductive pads 52 is created, with a minimal acoustical reflection at the center frequency of the array.

Figure 4:
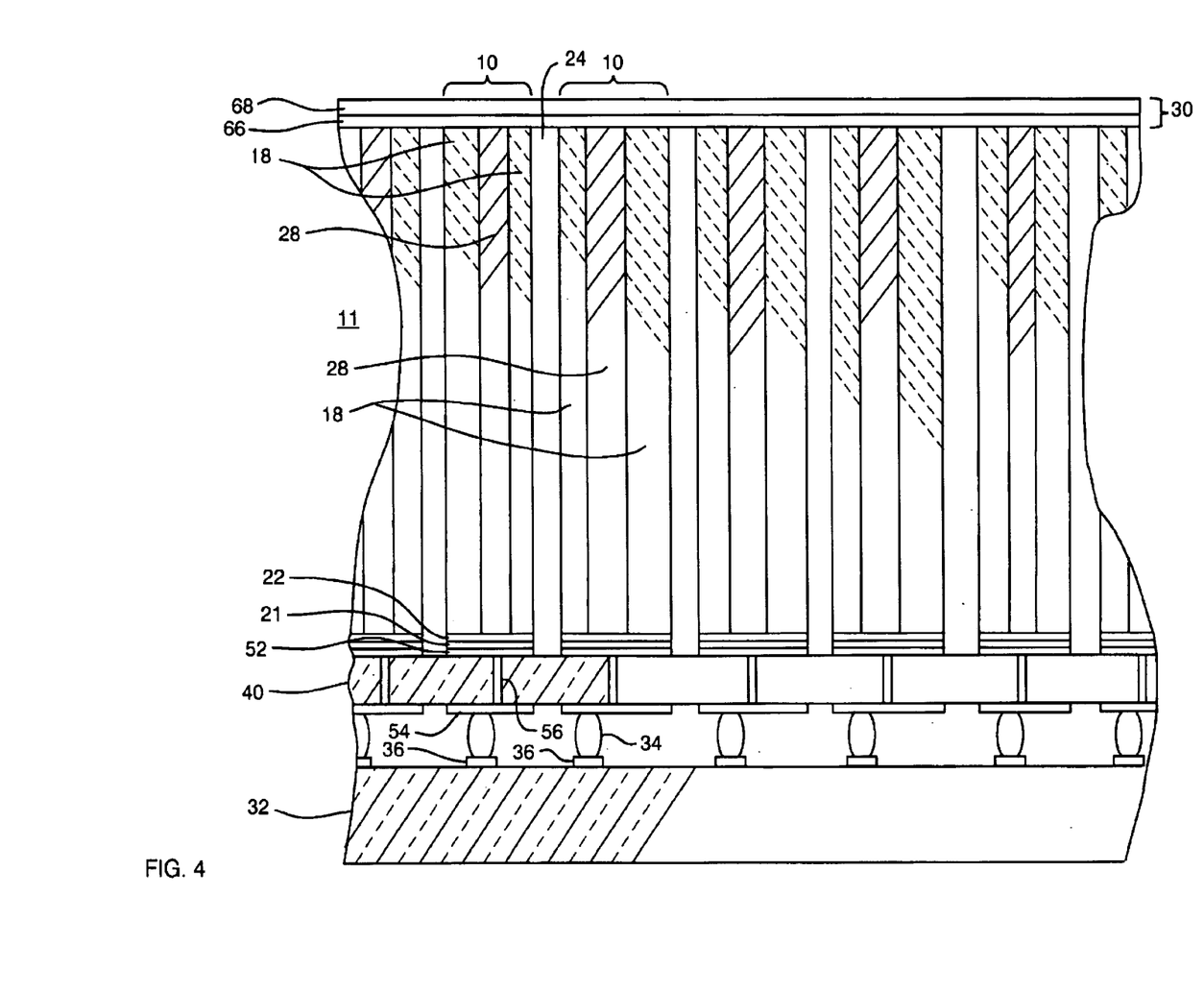
FIG. 4 is a diagrammatic cross-section view of the embodiment of FIG. 3, with a two part common electrode layer also functioning as an acoustical matching layer.

Referring now to FIG. 4, in a preferred embodiment, an electrically conductive layer 66 of prescribed thickness forms part of common electrode 30 of array 11. Attached to layer 66 is a second layer 68, also of prescribed thickness, and which may be conductive or non-conductive. The thickness and acoustical properties of these two layers are chosen to form acoustical matching layers as is well known in the art. These layers may be bonded with very thin layers of epoxy or other suitable bonding material to form common electrode 30 having enhanced acoustical properties. This thin, common electrode may be somewhat flexible so as not to contribute significant shear force at the element connections to the integrated circuit.

In an alternate embodiment of the invention, layer 68 with integral conducting surface layer 66 forms common electrode 30 and is mechanically bonded to the front surface of array elements 10. The bonding material of layer 66 in this embodiment may be a thin layer of conductive epoxy providing the integral electrically conducting surface function of the common electrode. Layer 68 in this embodiment may be a plastic such as polyimide, polyethylene, or polycarbonate film with a deposited conducting layer 66 such as copper. These two layers preferably then serve as an acoustical matching layer between the piezocomposite and the acoustical medium as previously described, as well as a common electrode.

Referring again to FIG. 4, delineation of bottom electrodes 22, bonding layer 21 and metallization pads 52 may also be accomplished during the dicing of the original piezocomposite into array pillars 18. Spaces 24 also serve to reduce element-to-element crosstalk and inter-element signal interference. This is particularly effective when the space is air-filled, due to the large acoustical impedance mismatch between the piezocomposite array elements 10 and air.

Crosstalk is also determined by the choice of material and dimensions of interposed substrate 40. Materials such as aluminum nitride have a high velocity of sound, typically on the order of 10,000 meters per second. A substrate thickness less than a wavelength of sound at the center frequency of the array inhibits a sound wave from propagating from one element into substrate 40 and then into the adjacent element. For example, the wavelength in aluminum nitride at 5 MHz is 2 mm. A substrate 40 thickness of less than 2 mm, and preferably 1 mm or less, effectively isolates adjacent elements 10 of the array. This embodiment of the array has been constructed by the Applicant and tested over several temperature cycles of 29° C. (52° F.) without degradation.

Figure 5:
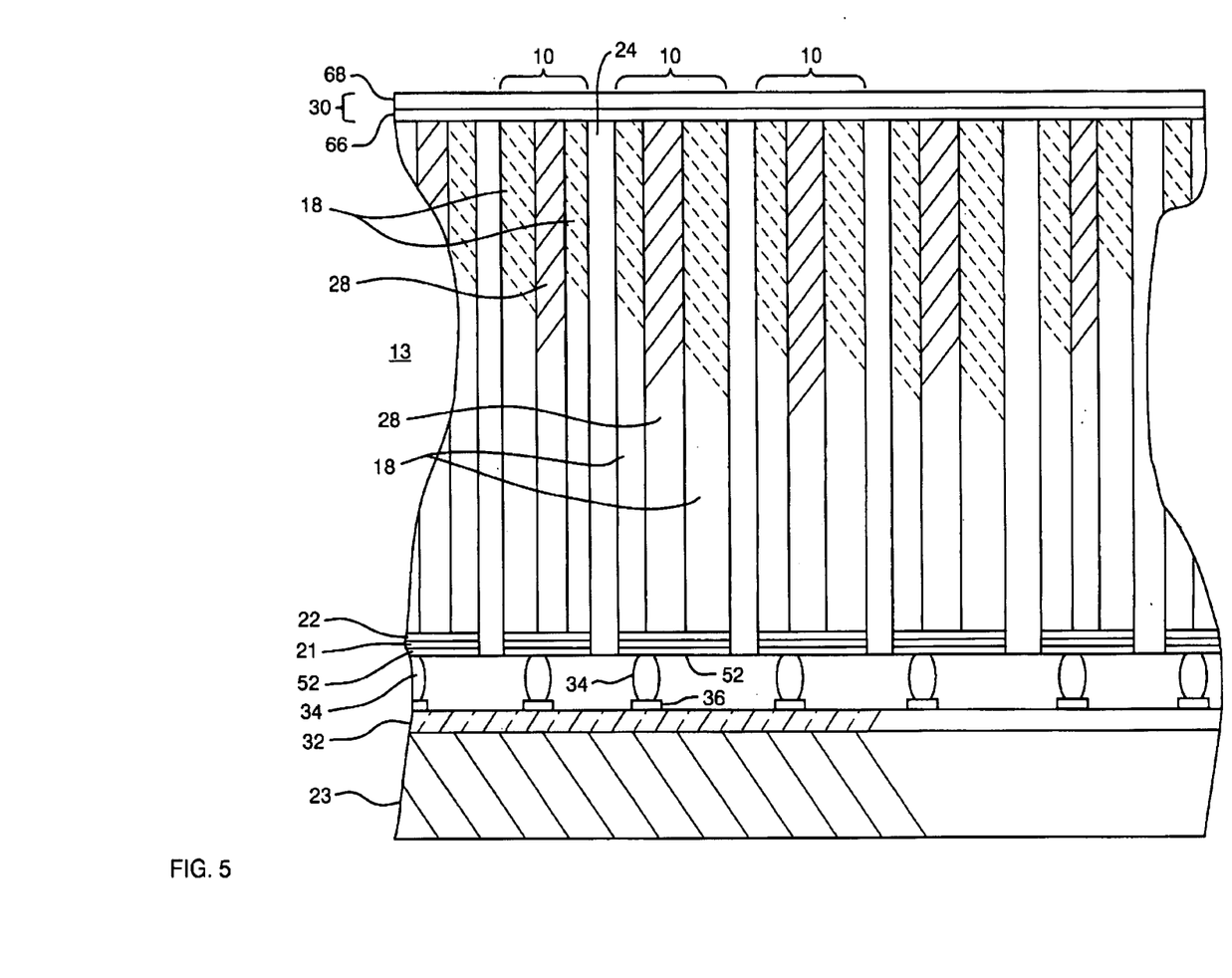
FIG. 5 is a diagrammatic cross-section view of another embodiment showing a transducer array with thinned interposed substrate bump bonded to a thinned semiconductor integrated circuit.
Figure 8:
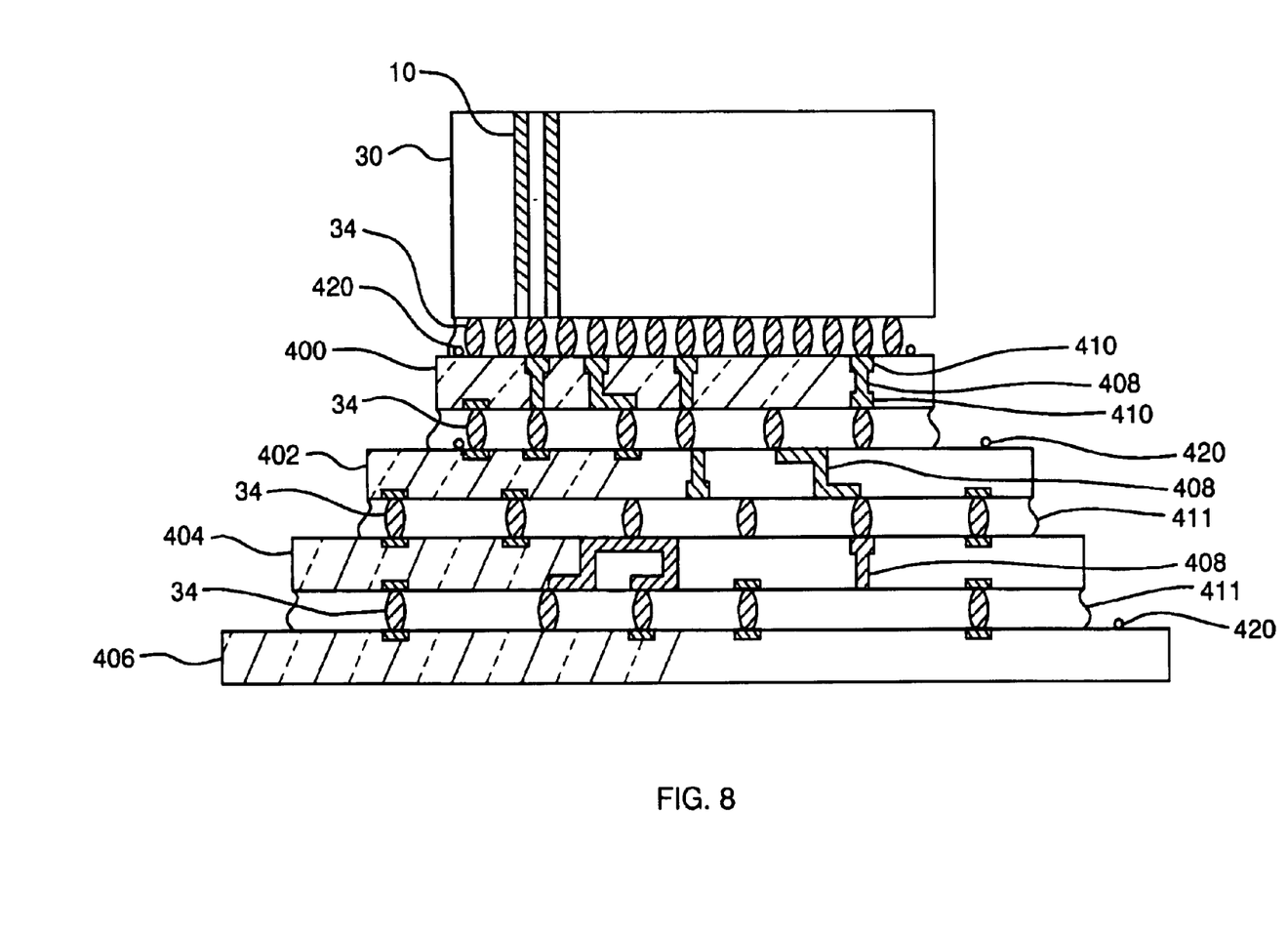
FIG. 8 is a diagrammatic cross-section view of a transducer array bump bonded to a multi-layered semiconductor substrate of thinned layers.

Referring to FIG. 5, a further aspect of the invention is a construction method using a thinned integrated circuit 32 in an integrated array 13, attached to array 13 at pads 52 and 36 by solder bumps 34. Solder bumps 34 have a diameter of less than one wavelength, in this embodiment about one tenth wavelength, of the center frequency of the array, so as to enhance vertical acoustical isolation of the respective element. Integrated circuit 32 conforms to the description of interposed substrate 40 of FIG. 6, with regard to thickness and acoustical properties by thinning the substrate to less than a wavelength, and preferably less than half of the wavelength of the center frequency, and thus becomes essentially acoustically transparent, providing lateral acoustical isolation between elements in tandem with the vertical isolation provided by the solder bumps 34. This technique of using a thinned IC minimizes crosstalk between elements 10 and enables wide bandwidth transducers. As described above, acoustical transparency requires the thickness of integrated circuit 32 to be selected to produce a minimum reflection at the center frequency of the transducer array, less than one wavelength and preferably less than about one half wavelength of the center frequency of the array. A thinned IC also facilitates the use of conventional ultrasound transducer designs including an acoustically attenuating backing structure 23, which are well known in the ultrasonic transducer art. Referring to FIG. 8, the thinned IC technique with its acoustical benefits is equally applicable to the multi-layered IC components of transducer arrays described at length in parent applications and again herein.

Figure 6:
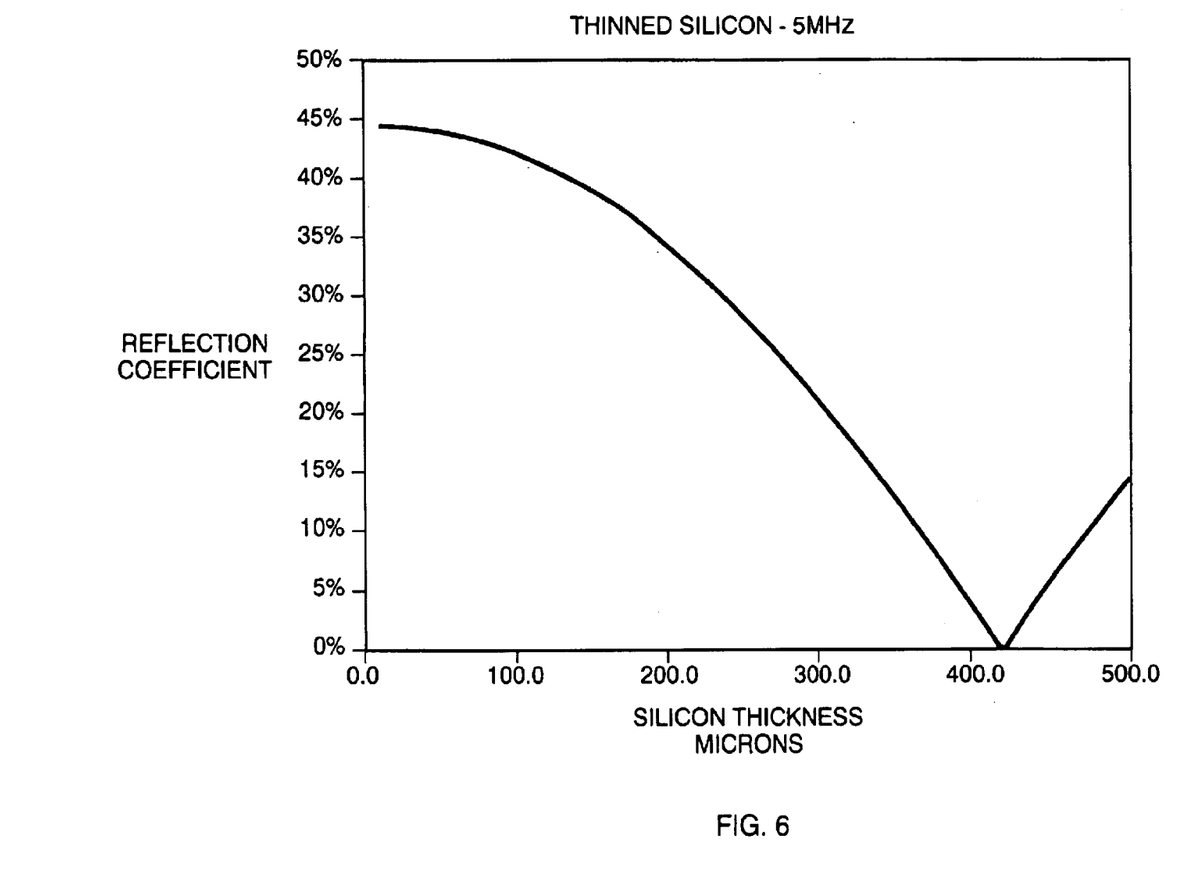
FIG. 6 is a chart of percentage of reflection coefficient versus silicon thickness of a substrate at a 5 MHz signal frequency.

FIG. 6 is a graph of the calculated sound transmission through a silicon layer of a transducer array and IC assembly, as a function of thickness, at 5 MHz. The silicon layer is sandwiched between a piezocomposite transducer of acoustical impedance=31.6 MRayls and a backside layer of a mixture of tungsten and epoxy, a commonly used formulation for an attenuating backing structure. This example uses a mixture of Echogel 1265 and fine tungsten powder, with acoustical impedance of 12.2 MRayls. The piezocomposite transducer is bonded to the silicon layer with a very thin layer of epoxy resin, such as Dow Chemical DER 332, which may be wicked into the airspace of a bump bonded joint after assembly as is known in the art. The thickness of this bonding layer was about the same as the dimensions of micro solder balls, 0.01 mm. This extremely thin layer is also acoustically transparent and could be neglected in the calculations for FIG. 8. It will be seen that the reflection coefficient goes to zero at about 420 microns thickness.

Figure 7:
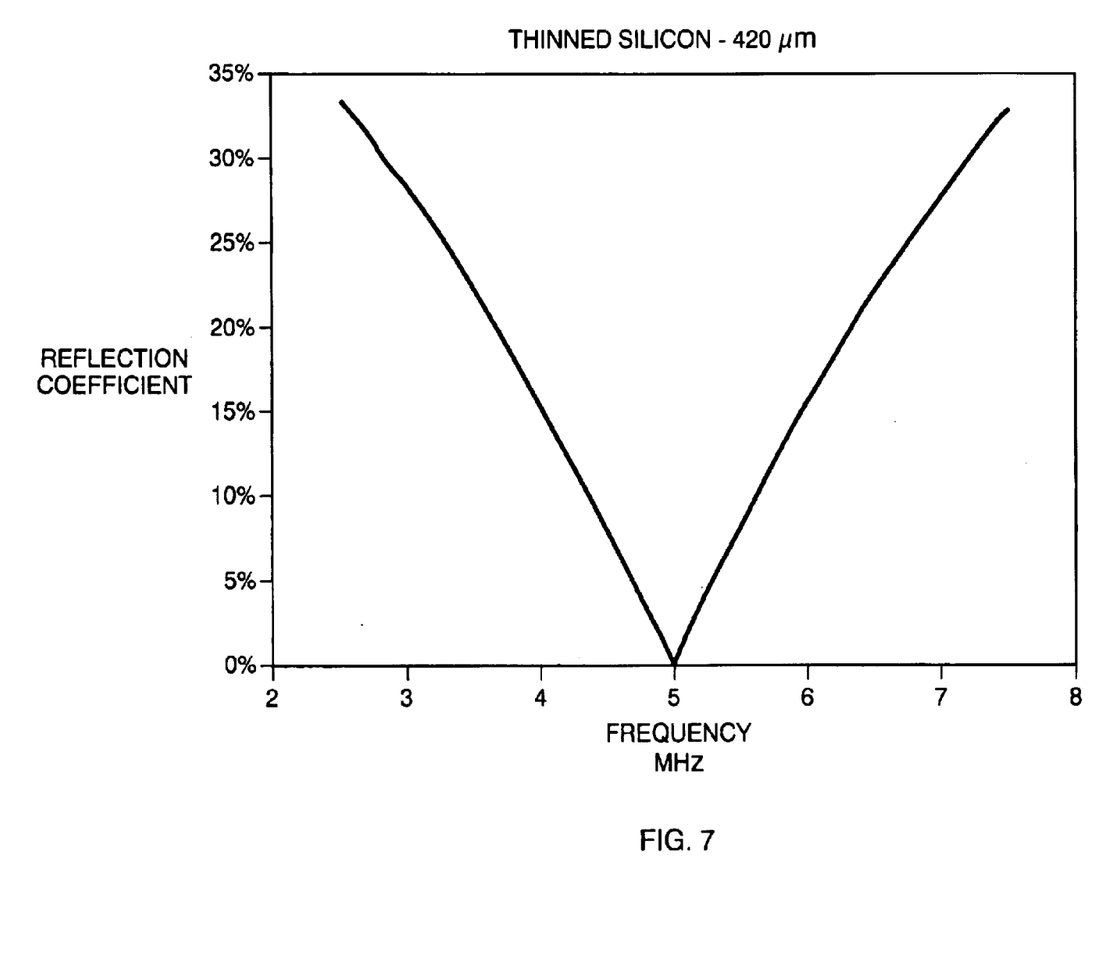
FIG. 7 is a chart of percentage of reflection versus frequency for a silicon substrate of 420 micrometer thickness.

FIG. 7 shows the same calculation of reflection coefficient vs. frequency for 420 $\mu$m (0.0165 in.) thick silicon. At higher frequencies, the silicon must be thinned inversely proportional to the frequency to accomplish the same goal. Thus at 10 MHz, the optimum thickness of the silicon layer would be 210 $\mu$m. This range of thickness is well within the state of the art in silicon thinning. For example, there is available equipment that plasma polishes silicon down to 50 $\mu$m (0.002) inches thickness.

FIG. 8 is a diagrammatic cross-section view of an athermal piezocomposite acoustical transducer array and multi-layered integrated circuit assembly embodiment of the invention. Array 30 is constructed in accordance with the invention to minimize acoustical crosstalk and interference between elements 10, as described above. There are four thinned integrated circuit layers or substrates 400, 402, 404 and 406, respectively, electrically connected to each other and to array 30 in accordance with the invention and the techniques described in the parent applications, using electrically conductive micro-bumps 34, electrically conducting vias 408 connecting substrates 400–406 at interconnect pads 410 on the top and/or bottom sides of substrates 400–406. The functionality of the IC is divided among substrates 400, 402, 404, and 406 as described in the parent applications. The performance of the device with respect to acoustical crosstalk and interference benefits from the several techniques of the instant invention.

The invention is susceptible of many other embodiments, all within the scope of the claims that follow. For example, there is an athermal piezocomposite acoustical transducer array and integrated circuit assembly consisting of a multiplicity of piezocomposite transducer elements of uniform element height arranged in an array pattern of uniform element width and uniform element length. The elements have a base end and a distal end and are separated from each other by spaces thorough the dicing process. There is a supporting substrate to which the base ends of the elements are attached, and a common electrode layer to which the distal end of the elements are attached.

There is a semiconductor integrated circuit attached to the supporting substrate by solder bumps, and electrically connected to the elements by conducting vias through the supporting substrate. The supporting substrate has a coefficient of thermal expansion approximating that of the integrated circuit. It has a thickness of less than one wavelength and preferably less than one half wavelength of the midrange frequency of the array. The solder bumps have a diameter of less than one wavelength, preferably less than about one half wavelength and most preferably less than about one tenth wavelength of the midrange or center frequency of the array. The spaces between the elements are filled with a non-conductive, acoustically attenuating material of lower elastic modulus than the transducer elements, so as to allow the elements to expand with temperature, yet not stress the solder bumps.

The acoustically attenuating material may be air. The supporting substrate may be aluminum nitride ceramic. The supporting substrate may have metallic top and bottom pads and interconnecting conductive vias. The base ends of the elements are attached to the supporting substrate with silver epoxy in some cases, but are attached in other embodiments with non-conductive epoxy so as to form parallel plate capacitors tuned for passing the center or midrange frequency of the array.

The common electrode layer of the array consists of a first electrically conductive layer of prescribed thickness and a second layer of prescribed thickness, where the first and second layer in combination are selected as an acoustical matching layer between the elements and the acoustical medium to which the transducer array is being applied. The second layer may be a plastic film, and the first layer may be a metallic coating layer deposited on the plastic film. The plastic film may be polyimide, polyethylene or polycarbonate, or another suitable plastic.

The semiconductor integrated circuit may have been thinned according to the theory of the invention, to a thickness of less than a wave length, or preferably less than one half wavelength of the center or midrange frequency of the array, in order to attenuate lateral transfer of acoustical signals from element circuit to element circuit that may have penetrated vertically from an element through the bond between the array and the IC, into the IC.

There may be a thinned first layer of integrated circuitry for operating the array where the first layer has a first side with electrical contacts for contacting the supporting substrate and a second side with second side electrical circuit contacts, and there may be a final layer of additional integrated circuitry for operating the array, where the final layer has at least a first side with matching electrical contacts, the layers are configured as successive layers from the first to the final layer, and the second side electrical contacts are electrically bonded to respective matching electrical contacts on the adjacent layer. There may be at least one intermediate layer with further associated integrated circuitry for operating the array, where the intermediate layer has a first side with matching electrical contacts and a second side with second side electrical contacts, and the intermediate layer is disposed between the first layer and the final layer.

As another example within the scope of the invention, there may be an athermal piezocomposite acoustical transducer array and integrated circuit assembly with a multiplicity of vertical piezoelectric members grouped into a spaced array of piezocomposite transducer elements of uniform element height arranged in a pattern of uniform element width and uniform element length. The elements have a base end and a distal end and are separated from each other by spaces. The base end of each element has a first conductive metallic pad contacting all the members of the element, and a second conductive metallic pad separated from the first pad by a non-conductive bonding layer where the pads and the bonding layer are configured together as a parallel plate capacitor for a minimum reflection at or near the center or midrange frequency of the array.

There is a common electrode layer to which the distal end of the elements are attached, and a thinned semiconductor integrated circuit for supporting the array, where the integrated circuit has a top side pattern of element contacts and is attached there at by solder bumps to the second metallic pads of the elements. The spaces between the elements are filled with a non-conductive acoustically attenuating material of lower elastic modulus than the transducer elements such that the coefficient of thermal expansion of the array is less than that of an element. The integrated circuit has a coefficient of thermal expansion approximating that of the array as a whole, and a thickness of less than one wavelength and preferably less than one half wavelength of the midrange frequency of the array. The solder bumps bonding the integrated circuit to the array have a diameter of less than one wavelength, preferably less than about one half wavelength, and most preferably less than about one tenth wavelength of the midrange frequency. The thinned semiconductor integrated circuit may have a backside layer of acoustically attenuating material.

Other and various equivalent embodiments within the scope of the claims that follow will be readily apparent to those skilled in the art, from the specification, abstract and figures included.

What is claimed is:

1. An athermal piezocomposite acoustical transducer array and integrated circuit assembly comprising:
   a multiplicity of piezocomposite transducer elements arranged in an array pattern, said elements having a base end and a distal end and being laterally separated from each other by spaces,
   a supporting substrate to which the base ends of said elements are attached,
   a common electrode layer to which the distal end of said elements are attached, and
   a semiconductor integrated circuit attached to said substrate by solder bumps and electrically connected to said elements by conducting vias through said supporting substrate, said substrate having a coefficient of thermal expansion approximating that of said integrated circuit and a thickness of less than one wavelength and preferably less than one half wavelength of the midrange frequency of said array, said solder bumps having a diameter of less than one wavelength, preferably less than about one half wavelength and most preferably less than about one tenth wavelength, of said midrange frequency, said spaces being filled with a non-conductive, acoustically attenuating material of lower elastic modulus than the transducer elements.

2. An athermal piezocomposite acoustical transducer array and integrated circuit assembly according to claim 1, said acoustically attenuating material comprising air.

3. An athermal piezocomposite acoustical transducer array and integrated circuit assembly according to claim 1, said supporting substrate comprising aluminum nitride ceramic.

4. An athermal piezocomposite acoustical transducer array and integrated circuit assembly according to claim 3, said supporting substrate comprising metallic top and bottom pads and interconnecting conductive vias.

5. An athermal piezocomposite acoustical transducer array and integrated circuit assembly according to claim 1, said base ends of said elements attached to said supporting substrate with silver epoxy.

6. An athermal piezocomposite acoustical transducer array and integrated circuit assembly according to claim 1, said base ends of said elements attached to said supporting substrate with non-conductive epoxy.

7. An athermal piezocomposite acoustical transducer array and integrated circuit assembly according to claim 1, said common electrode layer comprising a first electrically conductive layer of prescribed thickness and a second layer of prescribed thickness, said first and second layer in combination selected as an acoustical matching layer between said elements and the acoustical medium to which the transducer array is being applied.

8. An athermal piezocomposite acoustical transducer array and integrated circuit assembly according to claim 7, said second layer comprising a plastic film, said first layer comprising a metallic coating layer deposited on said plastic film.

9. An athermal piezocomposite acoustical transducer array and integrated circuit assembly according to claim 8, said plastic film comprising at least one plastic from among the group of plastics consisting of polyimide, polyethylene and polycarbonate.

10. An athermal piezocomposite acoustical transducer array and integrated circuit assembly according to claim 1, said semiconductor integrated circuit comprising a thinned semiconductor integrated circuit.

11. An athermal piezocomposite acoustical transducer array and integrated circuit assembly according to claim 1, said semiconductor integrated circuit comprising
   a thinned first layer with associated electronic circuitry for operating the array, said first layer having a first side with electrical contacts for contacting said supporting substrate and a second side with second side electrical circuit contacts, and
   a final layer with additional associated electronic circuitry for operating the array, said final layer having at least a first side with matching electrical contacts, said layers of said electronic circuitry being configured as successive layers from said first layer to said final layer, said second side electrical contacts being electrically bonded to respective said matching electrical contacts on the adjacent said layer.

12. An athermal piezocomposite acoustical transducer array and integrated circuit assembly according to claim 11, further comprising at least one intermediate layer with further associated integrated circuitry for operating the array, said intermediate layer having a first side with matching electrical contacts and a second side with second side electrical contacts, said intermediate layer disposed between said first layer and said final layer.

13. An athermal piezocomposite acoustical transducer array and integrated circuit assembly according to claim 11, said thinned semiconductor integrated circuit further configured with a backside layer of acoustically attenuating material.

14. An athermal piezocomposite acoustical transducer array and integrated circuit assembly comprising:
- a multiplicity of vertical piezoelectric members grouped into a spaced array of piezocomposite transducer elements, said elements having a base end and a distal end and being separated from each other by spaces, said base end of each said element having a first metallic pad contacting all said members of said element and a second metallic pad separated from said first pad by a non-conductive bonding layer, said pads and said bonding layer configured as a parallel plate capacitor for a minimum reflection at the center frequency of said array,
- a common electrode layer to which the distal end of said elements are attached, and
- a thinned semiconductor integrated circuit for supporting said array, said integrated circuit having a top side pattern of element contacts and being attached there at by solder bumps to said second metallic pads of said elements, said spaces between said elements being filled with a non-conductive acoustically attenuating material of lower elastic modulus than the transducer elements such that said coefficient of thermal expansion of said array is less than a said element, said integrated circuit having a coefficient of thermal expansion approximating that of said array and a thickness of less than one wavelength and preferably less than one half wavelength of the midrange frequency of said array, said solder bumps having a diameter of less than one wavelength, preferably less than about one half wavelength, and most preferably less than about one tenth wavelength of said midrange frequency.

15. An athermal piezocomposite acoustical transducer array and integrated circuit assembly according to claim 14, said thinned semiconductor integrated circuit further configured with a backside layer of acoustically attenuating material.

16. An athermal piezocomposite acoustical transducer array and integrated circuit assembly according to claim 14, said semiconductor integrated circuit comprising
- a first thinned layer with associated electronic circuitry for operating the array, said first layer having said top side pattern of element contacts and a second side with second side electrical circuit contacts, and
- a final layer with additional associated electronic circuitry for operating the array, said final layer having at least a first side with matching electrical contacts, said layers of said electronic circuitry being configured as successive layers from said first layer to said final layer, said second side electrical contacts being electrically bonded to respective said matching electrical contacts on the adjacent said layer.

17. An athermal piezocomposite acoustical transducer array and integrated circuit assembly according to claim 16, further comprising at least one intermediate layer with further associated integrated circuitry for operating the array, said intermediate layer having a first side with matching electrical contacts and a second side with second side electrical contacts, said intermediate layer disposed between said first layer and said final layer.

18. An athermal piezocomposite acoustical transducer array and integrated circuit assembly comprising:
- a multiplicity of piezocomposite transducer elements arranged in an array pattern, said elements having a base end and a distal end and being separated from each other by spaces filled with air,
- a common electrode layer to which the distal end of said elements are attached,
- a supporting substrate with metallic top and bottom pads connected by conducting vias, the base ends of said elements being attached to said top pads with silver epoxy, and
- a semiconductor integrated circuit attached to the bottom pads of said substrate by solder bumps and electrically connected to said elements by said conducting vias, said supporting substrate having a coefficient of thermal expansion approximating that of said integrated circuit and a thickness of less than one wavelength and preferably less than about one half wavelength of the midrange frequency of said array, said solder bumps having a diameter of less than one wavelength, preferably less than one half wavelength and most preferably less than about one tenth wavelength of said midrange frequency.

19. An athermal piezocomposite acoustical transducer array and integrated circuit assembly according to claim 18, said supporting substrate comprising aluminum nitride ceramic.

20. An athermal piezocomposite acoustical transducer array and integrated circuit assembly according to claim 18, said common electrode layer comprising a first electrically conductive layer of prescribed thickness and a second layer of prescribed thickness, said first and second layer in combination selected as acoustical matching layers between said elements and the acoustical medium.

21. An athermal piezocomposite acoustical transducer array and integrated circuit assembly according to claim 18, said semiconductor integrated circuit comprising a thinned integrated circuit.

22. An athermal piezocomposite acoustical transducer array and integrated circuit assembly according to claim 21, said thinned semiconductor integrated circuit further configured with a backside layer of acoustically attenuating material.

23. An athermal piezocomposite acoustical transducer array and integrated circuit assembly according to claim 18, said semiconductor integrated circuit comprising
- a first thinned layer with associated electronic circuitry for operating the array, said first layer having said top side pattern of element contacts and a second side with second side electrical circuit contacts, and
- a final layer with additional associated electronic circuitry for operating the array, said final layer having at least a first side with matching electrical contacts, said layers of said electronic circuitry being configured as successive layers from said first layer to said final layer, said second side electrical contacts being electrically bonded to respective said matching electrical contacts on the adjacent said layer.

24. An athermal piezocomposite acoustical transducer array and integrated circuit assembly according to claim 23, further comprising at least one intermediate layer with further associated integrated circuitry for operating the array, said intermediate layer having a first side with matching electrical contacts and a second side with second side electrical contacts, said intermediate layer disposed between said first layer and said final layer.

* * * * *